(12) United States Patent
Ghike et al.

(10) Patent No.: US 11,850,567 B2
(45) Date of Patent: Dec. 26, 2023

(54) APPARATUS FOR CONTINUOUS GRANULATION OF POWDER MATERIAL

(71) Applicant: Steerlife India Private Limited, Bangalore (IN)

(72) Inventors: Radhika Ghike, Bangalore (IN); Vijay Kulkarni, Bangalore (IN); Indu Bhushan, Bangalore (IN); Himadri Sen, Bangalore (IN); Babu Padmanabhan, Bangalore (IN); Vinay Rao, Bangalore (IN)

(73) Assignee: STEERLIFE INDIA PRIVATE LIMITED, Bangaluru (IN)

( * ) Notice: Subject to any disclaimer, the term of this patent is extended or adjusted under 35 U.S.C. 154(b) by 717 days.

(21) Appl. No.: 17/007,641

(22) Filed: Aug. 31, 2020

(65) Prior Publication Data
US 2021/0046439 A1 Feb. 18, 2021

Related U.S. Application Data

(62) Division of application No. 15/747,021, filed as application No. PCT/IB2016/054616 on Aug. 1, 2016, now Pat. No. 10,792,634.

(30) Foreign Application Priority Data

Jul. 31, 2015 (IN) .......................... 3986/CHE/2015

(51) Int. Cl.
*B01J 2/20* (2006.01)
*B29C 48/92* (2019.01)
(Continued)

(52) U.S. Cl.
CPC . *B01J 2/20* (2013.01); *A61J 3/02* (2013.01); *A61K 9/1652* (2013.01);
(Continued)

(58) Field of Classification Search
CPC .. B29B 7/489; B29B 9/06; B29B 9/08; B29B 9/12; B29B 7/482; B29B 7/483;
(Continued)

(56) References Cited

U.S. PATENT DOCUMENTS 4,786,514 A * 11/1988 Wiedmann ............ B29C 48/405
426/449
5,595,696 A 1/1997 Schlarb et al.
(Continued)

FOREIGN PATENT DOCUMENTS

EP 3219460 B1 * 12/2021 ............... B29B 7/48
EP 3328603 B1 * 4/2022 ................ A61J 3/02
(Continued)

OTHER PUBLICATIONS

Shanmugam, "Granulation techniques and technologies: recent progresses," Feb. 18, 2015, 9 pages.
(Continued)

*Primary Examiner* — Jose A Fortuna
(74) *Attorney, Agent, or Firm* — HANLEY, FLIGHT & ZIMMERMAN LLC

(57) ABSTRACT

A co-rotating twin screw processor for preparing dry granules including an input zone having one or more powder feeders for feeding an input material into the processor, a steam feeder configured to introduce steam as a granulation activating agent in to the processor, a granulation zone for granulating the input material in the presence of steam to form granules, a controller configured to control operation and feed rate of at least one of the powder feeder or the steam feeder such that 2.5 to 5 percent w/w of the steam with respect to the input material is available for granulation, and a discharge zone haring a non-extruding opening for collecting dry granules.

9 Claims, 2 Drawing Sheets

(51) Int. Cl.
  *A61K 9/16* (2006.01)
  *A61J 3/02* (2006.01)
  *B29C 48/405* (2019.01)
  *B29C 48/40* (2019.01)
  *B01J 2/28* (2006.01)
  *B01J 2/30* (2006.01)
  *B29B 9/06* (2006.01)
  *B29C 48/57* (2019.01)
  *B29C 48/04* (2019.01)
  *B29C 48/59* (2019.01)

(52) U.S. Cl.
  CPC .......... *A61K 9/1694* (2013.01); *B01J 2/28* (2013.01); *B01J 2/30* (2013.01); *B29C 48/40* (2019.02); *B29C 48/405* (2019.02); *B29C 48/92* (2019.02); *B29B 9/06* (2013.01); *B29C 48/04* (2019.02); *B29C 48/57* (2019.02); *B29C 48/59* (2019.02); *B29C 2948/926* (2019.02); *B29C 2948/92723* (2019.02)

(58) Field of Classification Search
  CPC ....... B29C 48/04; B29C 48/405; B29C 48/40; B29C 48/57; B29C 48/625; B29C 48/92; B29C 2948/926; B29C 2948/92723; B29C 48/59; A61J 3/02; A61K 9/1652; A61K 9/1694; B01J 2/20; B01J 2/28; B01J 2/30
  See application file for complete search history.

(56) References Cited

U.S. PATENT DOCUMENTS

| | | | |
|---|---|---|---|
| 5,772,721 A | 6/1998 | Kazemzadeh | |
| 5,786,445 A | 7/1998 | Wulff et al. | |
| 5,911,928 A | 6/1999 | Shimazu et al. | |
| 6,117,451 A | 9/2000 | Kumar | |
| 6,220,745 B1 | 4/2001 | Kobayashi et al. | |
| 6,287,496 B1 | 9/2001 | Lownds | |
| 6,499,984 B1 | 12/2002 | Ghebre-Sellassie et al. | |
| 6,688,217 B2* | 2/2004 | Hauck .................. | B29B 7/484 100/145 |
| 6,783,270 B1* | 8/2004 | Padmanabhan ......... | B29B 7/483 366/85 |
| 6,833,096 B2* | 12/2004 | Wang .................... | B29C 48/254 264/102 |
| 7,910,030 B2* | 3/2011 | Remon .................. | B29C 48/92 264/109 |
| 8,231,375 B2 | 7/2012 | Remon et al. | |
| 8,236,215 B2 | 8/2012 | Galimberti et al. | |
| 8,973,853 B2 | 3/2015 | Pierini et al. | |
| 9,205,027 B2* | 12/2015 | Kessler ................. | B29C 48/08 |
| 9,414,992 B2* | 8/2016 | Kessler ................. | B29C 48/08 |
| 9,956,709 B2* | 5/2018 | Padmanabhan ......... | B29C 48/00 |
| 10,759,876 B2* | 9/2020 | Savich ................... | B29C 48/65 |
| 10,786,459 B2* | 9/2020 | Upadhye .............. | B29C 48/2561 |
| 10,792,634 B2* | 10/2020 | Ghike ................... | B29B 7/483 |
| 11,247,378 B2* | 2/2022 | Bhushan ............... | B29B 7/94 |
| 11,247,379 B2* | 2/2022 | Bhushan ............... | B29C 48/57 |
| 11,247,380 B2* | 2/2022 | Bhushan ............... | B29C 48/57 |
| 11,529,313 B2* | 12/2022 | Upadhye .............. | A61K 9/1682 |
| 2003/0102584 A1 | 6/2003 | Leeners et al. | |
| 2003/0112698 A1* | 6/2003 | Hauck .................... | B29B 7/489 366/85 |
| 2003/0116034 A1* | 6/2003 | Hauck .................... | B29B 7/489 100/146 |
| 2006/0079432 A1 | 4/2006 | Weuthen et al. | |
| 2006/0108706 A1 | 5/2006 | Galimberti et al. | |
| 2006/0241213 A1 | 10/2006 | Galimberti et al. | |
| 2007/0167339 A1 | 7/2007 | Birch et al. | |
| 2007/0298082 A1* | 12/2007 | Fajt ...................... | A23N 17/005 426/601 |
| 2008/0056058 A1 | 3/2008 | Padmanabhan | |
| 2015/0029812 A1* | 1/2015 | Shimizu ................ | B29B 7/845 366/85 |
| 2016/0082640 A1* | 3/2016 | Padmanabhan ......... | B29C 48/40 425/8 |
| 2017/0319486 A1 | 11/2017 | Updahye et al. | |
| 2018/0200938 A1* | 7/2018 | Padmanabhan ......... | B29C 48/82 |
| 2018/0214835 A1* | 8/2018 | Ghike ................... | B29B 7/482 |
| 2019/0134875 A1 | 5/2019 | Bhushan et al. | |
| 2019/0263042 A1 | 8/2019 | Bhushan et al. | |
| 2019/0263043 A1 | 8/2019 | Bhushan et al. | |
| 2021/0046439 A1* | 2/2021 | Ghike ....................... | B01J 2/20 |

FOREIGN PATENT DOCUMENTS

| | | | |
|---|---|---|---|
| ES | 2915324 T3 * | 6/2022 | .............. A61J 3/02 |
| WO | 2017021864 | 2/2017 | |
| WO | WO-2017021864 A1 * | 2/2017 | .............. A61J 3/02 |
| WO | 2017183006 | 10/2017 | |

OTHER PUBLICATIONS

Ullah et al., "Moisture-Activated Dry Granulation—Part I: A Guide to Excipient and Equipment Selection and Formulation Development," Nov. 2, 2009, 5 pages.

Yousefi et al., "Effect of carrier type and spray drying on the physicochemical properties of powdered and reconstituted pomegranate juice," Dec. 25, 2010, 9 pages.

International Searching Authority, "International Search Report", issued in connection with PCT patent application No. PCT/IB16/54616, dated Dec. 7, 2016, 2 pages.

International Searching Authority, "Written Opinion", issued in connection with PCT patent application No. PCT/IB16/54616, dated Dec. 7, 2016, 7 pages.

Crouter et al, "The Effect of Moisture on the Flowability of Pharmaceutical Excipients," Feb. 1, 2014, 10 pages.

United States Patent and Trademark Office, "Restriction Requirement," issued in connection with U.S. Appl. No. 15/747,021, dated Sep. 12, 2019, 7 pages.

United States Patent and Trademark Office, "Non-Final Office action," issued in connection with U.S. Appl. No. 15/747,021, dated Jan. 3, 2020, 15 pages.

United States Patent and Trademark Office, "Notice of Allowance," issued in connection with U.S. Appl. No. 15/747,021, dated Jun. 1, 2020, 8 pages.

* cited by examiner

APPARATUS FOR CONTINUOUS GRANULATION OF POWDER MATERIAL

RELATED APPLICATIONS

This patent arises from a divisional of U.S. patent application Ser. No. 15/747,021, which was filed on Jan. 23, 2018, now U.S. Pat. No. 10,792,634 B2, which is the U.S. national stage of International Patent Application Serial No. PCT/IB2016/054616, having an international filing date of Aug. 1, 2016, and claims benefit of Indian Patent Application No. 3986/CHE/2015, filed on Jul. 31, 2015, all of which are hereby incorporated by reference in their entireties for all purposes.

FIELD OF THE INVENTION

The present disclosure relates to the field of granulation. More specifically, it relates to a continuous, efficient and cost-effective process for granulation of powder materials. The present disclosure also relates to a twin screw processor for continuous granulation of the powder materials.

BACKGROUND

Granulation is a process of size enlargement of powder material and is utilized in various industries like pharmaceutical, agricultural, cosmetic, pesticide, food, detergents etc. Particularly in pharmaceutical industry, granulation is used to process powders into dosage forms like tablets and capsules.

The granulation process converts powders into similarly sized granules while reducing the content of fines or dust particles in the final product. Accordingly, the characteristics of an ideal granule include improved flow properties, content uniformity due to a narrow distribution of particles and optimum strength to withstand storage, transportation and packaging stresses. In cases where granules are to be tableted, compressibility also becomes important. The granule compressibility is ensured by an optimum particle size distribution and presence of right amount of fines to enable compression and compaction of the granules.

Conventionally, granulation methods are divided into dry granulation and wet granulation methods. Granulation methods may be further classified as batch or continuous methods.

Moisture-Activated Dry Granulation (MADG) is a batch process typically carried out in a high shear granulator that is a variation of the conventional wet granulation method that works by limiting the amount of water with the objective of eliminating a heat based drying step. The process comprises (1) an agglomeration stage and (2) a moisture absorption/distribution stage. The process involves adding of small quantities of water, to a powder mix comprising one or more active ingredient(s), binder(s) and other excipients to effect agglomeration, followed by mixing. After agglomeration, a moisture absorbing excipient is added to the mixture to absorb excess moisture and to redistribute the moisture to comparatively dry the granules. The dry granular mass so obtained requires a further sizing step to obtain desired granule size. It is an essential requirement of the MADG process to employ equipment such as a high-shear granulator and an airless spray system to ensure proper mixing and uniform granulation. These conventional granulators have dead spots where material could stick. High-drug load formulations are particularly difficult to develop by conventional MADG process owing to the high shear mixing and complex equipment requirement. Keeping the ratio of granulating fluid to the blend being granulated constant throughout is also not possible. Thus, in spite of its known simplicity and advantages, MADG process has not been widely adopted by the pharmaceutical industry, as also discussed by Ullah et al., Pharm. Technol., 33(11), 62-70 (2009). A primary factor for this, according to Ullah et al. is the uncertainty about equipment specifications and ambiguity about the manufacturing process. Another concern is that the MADG process is a batch process.

U.S. Pat. Nos. 7,910,030 and 8,231,375 disclose a continuous wet granulation process using a twin screw apparatus. The disclosed process involves using an aqueous granulating liquid in a concentration of 7.5% to 8.5% by weight of the powder material. The process requires a drying step to remove excess granulating liquid added after the granules are discharged from the processor.

The conventional granulation methods suffer from various disadvantages. These methods may suffer from batch-to-batch variability of granule properties like friability and porosity depending on the physical properties of the input materials. For granules prepared by wet granulation method, the granule properties may further depend on factors like volume of the binder, wet-massing time, amount of shear applied and drying rate of wet granules. The conventional granulators or equipments used for granulation may also show presence of dead spots leading to non-uniform distribution of granulating fluid. The methods require drying the granules, at a temperature as high as 60° C. Even those granulation processes that use small quantities of a granulating liquid require a separate drying step, adding to complexity of the process and additional equipment requirement for drying. Consequently, the methods give lower yields and inconsistent granule properties. Further, such methods remain unsuitable for granulation of heat sensitive and moisture sensitive ingredients.

SUMMARY OF THE INVENTION

A process for preparing granules in a co-rotating twin screw processor is disclosed. The process comprises feeding an input material for granulation in the processor using one or more powder feeders, introducing steam as a granulation activating agent in the processor, granulating the input material in presence of the steam to form granules, and optionally collecting the granules from a discharge zone of the processor, wherein feed rate of the steam into the processor is determined based on feed rate of the input material into the processor.

A co-rotating twin-screw processor for preparing granules is also disclosed. The processor comprises an input zone having one or more powder feeders for feeding an input material into the processor, a steam feeder configured to introduce steam as a granulation activating agent in to the processor, a granulation zone for granulating the input material in presence of steam to form granules, a controller configured to control operation and feed rate of at least one of the powder feeder or the steam feeder such that 2.5 to 5 percent w/w of the steam with respect to the input material is available for granulation, and a discharge zone having a non-extruding opening for collecting the granules.

DETAILED DESCRIPTION

Figure 1:
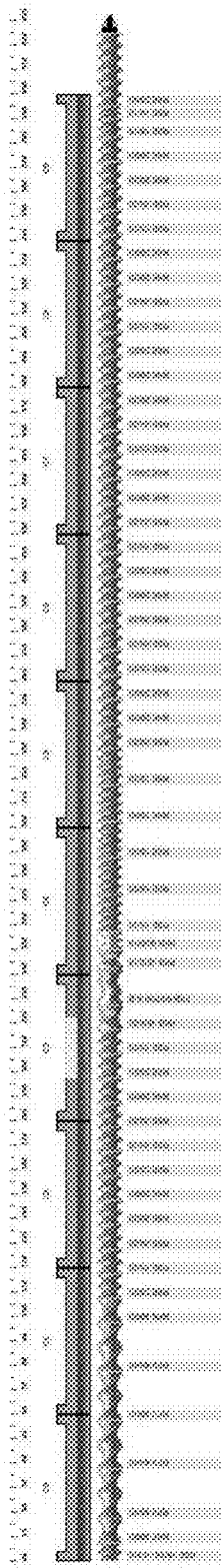
FIG. 1 illustrates the screw configuration of a co-rotating twin-screw processor in accordance with Example 1 of the present disclosure.

For the purpose of promoting an understanding of the principles of the invention, reference will now be made to embodiments and specific language will be used to describe the same. It will nevertheless be understood that no limitation of the scope of the invention is thereby intended, such alterations and further modifications in the disclosed process, disclosed processor, and such further applications of the principles of the invention therein being contemplated as would normally occur to one skilled in the art to which the invention relates.

It will be understood by those skilled in the art that the foregoing general description and the following detailed description are exemplary and explanatory of the invention and are not intended to be restrictive thereof.

Reference throughout this specification to "one embodiment" "an embodiment" or similar language means that a particular feature, structure, or characteristic described in connection with the embodiment is included in at least one embodiment of the present invention. Thus, appearances of the phrase "in one embodiment", "in an embodiment" and similar language throughout this specification may, but do not necessarily, all refer to the same embodiment.

Reference throughout this specification to "steam" or "vapor", unless otherwise mentioned should be construed to mean "water vapor" or "steam" devoid of organic solvents or organic solvent vapors.

The present disclosure relates to a continuous, efficient and cost-effective process for preparing granules from input material or powder materials. The granules obtained are suitable for formulating into pharmaceutical unit dosage forms like tablets and capsules. Further, the granules formed by the disclosed process possess critical attributes like ability to flow freely, compressibility, narrow particle size distribution and optimum strength. The present disclosure also relates to a twin screw processor for preparing granules from the powder materials.

The process comprises feeding an input material for granulation in a co-rotating twin-screw processor, introducing an optimal quantity of steam/vapor as a granulation activating agent in the processor sufficient to granulate the input material but not to over-wet it, granulating the input material in presence of steam to form granules and optionally collecting the granules from the processor. Feed rate of the steam into the processor is determined based on feed rate of the input material into the processor.

In accordance with an embodiment, the input material comprises one or more ingredient(s). The input material can also include one or more binder(s) and optionally one or more other excipient(s). By way of an example, the input material comprises one or more ingredient(s) and one or more binder(s).

In accordance with an embodiment, the feed rate of the steam in the processor is adjusted based on the feed rate of the input material into the processor. In accordance with an embodiment, the feed rate of the steam in the processor is adjusted based on the feed rate of the input material into the processor such that steam in an amount of about 2.5 to 5 percent w/w with respect to the input material is available for granulation.

In accordance with an embodiment, the feed rate of the steam in the processor is adjusted based on the feed rate of the input material into the processor such that steam in an amount of about 2.5 to 4 percent w/w with respect to the input material is available for granulation. In other embodiments, the feed rate of the steam in the processor is adjusted based on the feed rate of the input material into the processor such that steam in an amount of about 2.5 to 3 percent w/w with respect to the input material is available for granulation.

In accordance with an embodiment, the feed rate of the steam is constant for a fixed feed rate of the input material.

In accordance with an embodiment, the process comprises introducing 2.5 to 5 percent w/w of steam with respect to the input material. In accordance with an embodiment, the process comprises introducing 2.5 to 4 percent w/w of steam with respect to the input material. In other embodiments, the process comprises introducing 2.5 to 3 percent w/w of steam with respect to the input material.

Adding an optimal quantity of steam/vapor at a constant rate with respect to the feed rate of the input material, sufficient to granulate the input material but not to over-wet it ensures obtaining dry granules directly from the twin-screw processor without requiring any additional drying step. Granulation of the input material with a small quantity of steam/vapor is facilitated by use of high shear mixing elements such as fractional kneading elements in the granulation zone.

In accordance with an embodiment, the moisture content of the granules obtained from the twin-screw processor is not more than 5 percent w/w. In accordance with an embodiment, the moisture content of the granules obtained from the twin-screw processor is not more than 4 percent w/w. In accordance with an embodiment, the moisture content of the granules obtained from the twin-screw processor is not more than 3 percent w/w.

In accordance with an embodiment, the process comprises feeding the input material comprising one or more ingredient(s), optionally one or more binder(s) and optionally one or more other excipient(s) separately and mixing them in a specific ratio within the twin-screw processor. In accordance with an embodiment, the process comprises feeding the input material comprising one or more ingredient(s), optionally one or more binder(s) and optionally one or more other excipient(s) as a pre-mix blend into the processor.

In accordance with an embodiment, the granulation of some powder materials may require an addition of one or more moisture absorbing excipient(s) or moisture absorbent(s) to the granules obtained from the twin screw processor followed by mixing. In accordance with an embodiment, the addition of the one or more moisture absorbing excipient(s) and mixing is done within the twin-screw processor.

In accordance with an embodiment, the one or more moisture absorbing excipient(s) is fed into the processor after activation of the granulation of the input material with the steam.

In accordance with an embodiment, the one or more moisture absorbing excipient(s) is selected from microcrystalline cellulose, silicon dioxide or a combination thereof. In accordance with a specific embodiment, the moisture absorbing excipient is microcrystalline cellulose. By way of an example, the moisture absorbing excipient is microcrystalline cellulose having loss on drying not more than 1.5 percent w/w.

In accordance with an embodiment, the moisture absorbing excipient(s) may be added in an amount of about 5 to 20 percent w/w. In other embodiments, the moisture absorbing excipient(s) is added in an amount of about 10 to 20 percent w/w.

In accordance with an embodiment, the one or more moisture absorbing excipient(s) is fed into the twin screw processor through one or more excipient feeders separately. In accordance with an embodiment, the one or more moisture absorbing excipient(s) is fed into the twin screw processor as a pre-mix blend. The pre-mix blend may further comprise any one or more of the one or more ingredient(s), the one or more binder(s) and the one or more other excipient(s).

In accordance with an embodiment, the granules obtained by the process are mixed with conventionally known additives, modifiers or excipients and processed further into pharmaceutical dosage forms like tablets and capsules.

In accordance with an embodiment, the one or more ingredient(s) include active ingredient(s) that may be selected from a group including foodstuffs, mineral ores, agricultural products (e.g. fertilizers), detergents, catalysts, chemicals, as well as biologically active ingredients. In accordance with an embodiment, biologically active ingredients include Active Pharmaceutical Ingredients (APIs) and ingredients for cosmetic, veterinary and for plant use.

In accordance with an embodiment, the API is selected from drugs belonging to various therapeutic categories such as antiinfectives, antibacterial agents, antihistamines and decongestants, anti-inflammatory agents, antiparasitics, antivirals, antifungals, amoebicidals, or trichomonocidal agents, analgesics, antiarthritics, antipyretics, antiasthmatic agents, anticoagulants, anticonvulsants, antidepressants, antidiabetics, antineoplastics, antipsychotics, antihypertensives, expectorants, electrolytes, laxatives, phytopharmaceuticals, muscle relaxants and diuretics. In accordance with an embodiment, the API can be a combination of two or more drugs. The amount of the API may vary depending on various factors, for example, the intended therapeutic application, the dosage form etc.

In accordance with an embodiment, the binder(s) include potato, wheat or corn starch, hydroxypropyl cellulose, hydroxyethyl cellulose; hydroxypropyl methylcellulose, polyvinylpyrrolidone (PVP), guar gum, pectin, gelatin, sodium alginate and the like suitable for pharmaceutical use. In accordance with a specific embodiment, the binder is a polyvinylpyrrolidone like PVP K30.

The amount of the binder(s) may depend on the type and amount of the API and other ingredients. In accordance with an embodiment, the amount of the binder(s) may range from 2.5% to 5%.

In accordance with an embodiment, the one or more excipient(s) include any suitable pharmaceutically (or physiologically) acceptable excipients for use with APIs such as conventionally used disintegrants, lubricants, sweeteners, flavoring agents, taste masking agents, diluents, glidants, wetting agents, effervescent acid-base couple, colorants, or combinations thereof.

The process is carried out at a temperature less than 40° C. In accordance with a specific embodiment, the process is carried out at a temperature of about 30° C. In accordance with an embodiment, the process is carried out at low temperatures and a short residence time is maintained within the processor.

In accordance with an embodiment, the input material comprises moisture sensitive and/or heat sensitive ingredients.

Parameters like low residence time, low temperature within the processor and a process not requiring a separate thermal drying step are responsible for making the disclosed process suitable for granulation of an input material comprising moisture sensitive and/or heat sensitive ingredients.

In accordance with an embodiment, an organic solvent vapor or a mixture of organic solvent vapor and steam can also be used. However, use of these is not advisable as handling of such solvents is hazardous. Also since, drying of the granules is not being carried out post-processing by conventional means such as tray drying or drying in an oven, controlling the volatile impurities in the final product within limits should be considered.

A continuous process for granulation of the powder materials according to the present disclosure is ensured by the processor configuration designed as per the present disclosure.

In accordance with an embodiment, the co-rotating twin screw processor is a co-rotating twin screw extruder.

A co-rotating twin-screw processor for continuously preparing granules according to the present disclosure is also disclosed. The processor comprises an input zone having one or more powder feeders for feeding the input material, a steam feeder for configured to introduce steam as a granulation activating agent, a granulation zone for granulating the input material in presence of steam to form granules, and a discharge zone having a non-extruding opening for collecting the granules. The twin-screw processor further comprises a controller configured to control operation and feed rate of at least one of the powder feeder or the steam feeder such that 2.5 to 5 percent w/w of steam with respect to the input material is available to for granulation.

In accordance with an embodiment, the steam feeder is located in the granulation zone of the processor.

In accordance with an embodiment, the input zone comprises conveying elements only. In accordance with an alternate embodiment, the input zone comprises conveying and mixing elements.

In accordance with an embodiment, the input zone comprises powder feeders for feeding one or more ingredient(s), optionally one or more binder(s) and optionally one or more other excipients at different feed rates. In accordance with an embodiment, the input zone comprises powder feeders for feeding one or more ingredient(s), optionally one or more binder(s) and optionally one or more other excipients as one or more pre-mix blends.

Agglomeration and uniform distribution of the steam/vapor occurs simultaneously within the granulation zone of the twin-screw processor. The granulation zone of the twin-screw processor is also responsible for sizing of the granules without requiring a separate milling step. In accordance with an embodiment, the granulation zone comprises kneading elements for uniform distribution of the steam/vapor during granulation. In accordance with an embodiment, the granulation zone comprises fractional kneading elements as described in U.S. Pat. No. 6,783,270, incorporated here by reference.

In accordance with an embodiment, the granulation zone comprises not more than two pairs of fractional kneading elements for uniform distribution of the steam during granulation.

In accordance with an embodiment, the processor further comprises an excipient feeder for introducing one or more moisture absorbing excipient(s) into the processor downstream of the steam feeder.

In accordance with an embodiment, the processor further comprises a moisture distribution zone for mixing the one or more moisture absorbing excipient(s) with the granules from the granulation zone to obtain the granules having moisture content not more than 5 percent w/w. In other embodiments, the granules having moisture content not more than 3 percent w/w are obtained. In other embodiments, the granules having moisture content not more than 2 percent w/w are obtained.

In accordance with an embodiment, the moisture distribution zone comprises bilobed kneading elements. In accordance with yet another embodiment, the moisture distribution zone comprises one pair of fractional kneading elements.

In accordance with an embodiment, the controller is configured to control operation and feed rate of one or more of the powder feeder, the steam feeder or the excipient feeder such that moisture content of the granules obtained from the discharge zone is less than 5 percent w/w.

In accordance with an embodiment, the controller includes a micro-processor and a memory. The micro-processor comprises suitable logic, circuitry, interfaces, and/or code that may be configured to execute a set of instructions stored in the memory to control the operation and the feed rate of at least one of the powder feeder, the steam feeder or the excipient feeder. The micro-processor may be implemented based on a number of processor technologies known in the art. Examples of the micro-processor include, but not limited to, an X86-based processor, a Reduced Instruction Set Computing (RISC) processor, an Application-Specific Integrated Circuit (ASIC) processor, a Complex Instruction Set Computing (CISC) processor, and/or other processor. The memory is configured to store data including predetermined feed rates for one or more of the powder feeder, the steam feeder or the excipient feeder.

In accordance with an embodiment, the controller is configured to generate data including predetermined feed rates for one or more of the powder feeder, the steam feeder or the excipient feeder and store the data within the controller.

In accordance with an embodiment, the controller is configured to adjust rate of introduction of the steam in the processor based on feed rate of the input material into the processor such that 2.5 to 5 percent w/w of the steam with respect to the input material is available for granulation.

In accordance with an embodiment, barrel temperature of the twin-screw processor is less than 40° C. while carrying out the granulation. In accordance with a specific embodiment, the barrel temperature of the twin-screw processor is about 30° C. while carrying out the granulation.

In accordance with an embodiment, the twin-screw processor is provided with elements that ensure that there is no material stagnation and also ensure low residence times.

In accordance with an embodiment, the input material comprises moisture sensitive and/or heat sensitive ingredients.

In accordance with an embodiment, the co-rotating twin screw processor is a co-rotating twin screw extruder.

EXAMPLES

The following examples illustrate a process for preparing granules in a co-rotating twin-screw processor according to the present disclosure. The details of the experiments are provided below:

Example 1

TABLE 1

Composition of the Granules of Example 1

| Ingredients | Quantity (% w/w) |
|---|---|
| Paracetamol | 75 |
| Polyvinylpyrrolidone (PVP K30) | 2.5 |
| Microcrystalline cellulose (Avicel PH-200 LM) | 20 |
| Croscarmellose sodium | 2.5 |

Processor Configuration

The trials were performed using a co-rotating twin-screw extruder (Omega 20) designed by the applicant herein with screw configuration F1 illustrated in FIG. 1. The machine specification and the process parameters are described in Table 2, below:

TABLE 2

Configuration of the Twin-screw Processor of Example 1

| Machine Name | Omega 20 |
|---|---|
| L/D | 60 |
| Total no. of Barrels | 10 |
| Screw speed | 600 rpm |
| Element length | 1245 mm |
| Maximum Screw Speed | 1200 rpm |
| Maximum motor power | 13 Kw |
| Diameter | 19.6 mm |
| Percentage of kneading blocks | 6.4% |
| Feed Rate | 25.5 Hz (100.0 g of input blend/min) |
| Barrel Temperature | 30° C. |
| Steam Input | 2.5-3.5% w/w of input blend |

| Screw Elements | |
|---|---|
| 1. | RSE 15/15-1CHS |
| 2. | NRF 40/20 |
| 3. | RFV 40/40 |
| 4. | RFV 40/40 |
| 5. | RFV 40/40 |
| 6. | RFV 40/40 |
| 7. | RFN 40/20 |
| 8. | RSE 20/20 |
| 9. | RSE 20/20 |
| 10. | RSE 20/20 |
| 11. | RSE 20/20 |
| 12. | RSE 20/20 |
| 13. | RSE 20/20 |
| 14. | RSE 20/20 |
| 15. | RSE 20/20 |
| 16. | RSE 20/20 |
| 17. | RSE 20/20 |
| 18. | RSE 20/20 |
| 19. | RKB 45/5/20 |
| 20. | FKB 90/7/30 A, B |
| 21. | RKB 45/5/15 |
| 22. | NKB 90/5/15 |
| 23. | RSE 15/30 |
| 24. | RSE 15/30 |
| 25. | RSE 15/30 |
| 26. | RSE 15/30 |
| 27. | RSE 15/30 |
| 28. | RSE 20/20 |
| 29. | RSE 20/20 |
| 30. | RSE 20/20 |
| 31. | RSE 20/20 |
| 32. | RSE 20/20 |
| 33. | RSE 20/20 |
| 34. | RSE 20/20 |
| 35. | RSE 20/20 |
| 36. | RSE 20/20 |
| 37. | RSE 20/20 |
| 38. | RSE 20/20 |

TABLE 2-continued

Configuration of the Twin-screw Processor of Example 1

| | |
|---|---|
| 39. | RSE 20/20 |
| 40. | RSE 20/20 |
| 41. | RSE 20/20 |
| 42. | RSE 20/20 |
| 43. | RSE 20/20 |
| 44. | RSE 20/20 |
| 45. | RSE 20/20 |
| 46. | RSE 20/20 |
| 47. | RSE 20/20 |
| 48. | RSE 20/20 |
| 49. | RSE 20/20 |
| 50. | RSE 20/20 |
| 51. | RSE 20/20 |
| 52. | RSE 20/20 |
| 53. | RSE 15/15 |
| 54. | RSE 10/10 |
| 55. | RSE 20/60 |

List of Abbreviations for Elements

RSE Right Handed Screw Element

RFV Regular Flight Shovel Element

RFN Regular Flight Shovel Element to Normal

RKB Right Handed Kneading Block

FKB Forward kneading block

NKB Neutral kneading block

NRF Normal to RFV (transition element)

CHS Champer and Step

Process

An input blend comprising paracetamol, croscarmellose sodium and PVP K30 was prepared and fed into the input zone of the twin screw processor. A lab scale steam generator was used to generate steam which was introduced into the processor in an amount of 2.5%-3.5% w/w of the input blend. The blend was then processed as per the processor configuration given in Table 2 to obtain Paracetamol granules from the discharge zone of the processor. The moisture content of the granules was 2.52 percent w/w as determined by Loss on Drying (LOD) method.

The Paracetamol granules obtained from the processor were then mixed with Avicel PH-200 LM (LOD<1.5% w/w). The final granules obtained were collected and evaluated for moisture content and other critical attributes as given below.

Experimental Results

1. Moisture Content

The moisture content of the granules obtained after mixing with Avicel PH-200 LM was 1.55 w/w.

2. Granule Properties

Characterization of the granules was carried out by way of determination of particle size distribution, Bulk Density, Tapped Density, Carr's Index and Hausner Ratio. The results are as follows:

TABLE 3

Properties of the Granules of Example 1

| | |
|---|---|
| Bulk Density | 0.408 g/ml |
| Tapped Density | 0.574 g/ml |
| Carr's Index | 28.974% |
| Hausner Ratio | 1.407 |
| Angle of Repose | 26.656° |

TABLE 4

Particle Size Distribution of Granules of Example 1

| S. No. | Mesh size (μm) | Sieve No. | Wt. Retained particles (gm) | % Wt. Retained particles | % Cumulative Retained particles | % particles passed |
|---|---|---|---|---|---|---|
| 1. | 850 | #20 | 2.29 | 19.62 | 19.62 | 80.38 |
| 2. | 420 | #40 | 1.72 | 14.74 | 34.36 | 65.64 |
| 3. | 250 | #60 | 0.70 | 6.00 | 40.36 | 59.64 |
| 4. | 150 | #100 | 3.66 | 31.36 | 71.72 | 28.28 |
| | Base | | 2.99 | 25.62 | 97.34 | .66 |

Example 2

TABLE 5

Composition of Granules of Example 2

| Ingredients | Quantity (% w/w) |
|---|---|
| Metformin Hydrochloride | 70.0 |
| Polyvinylpyrrolidone (PVP K30) | 5.0 |
| Microcrystalline cellulose (Avicel PH-200 LM) | 20.0 |
| Croscarmellose sodium | 5.0 |

Procedure:

90% of the Metformin Hydrochloride was weighed and passed through mesh #20 to remove any lumps. PVP K30 was weighed and passed through mesh #60. Weighed quantity of PVP K30 was then added to the weighed quantity of Metformin Hydrochloride followed by thorough mixing. Mixing was done for about 2-3 min and the mixture was then stored in a tightly closed polybag as BLEND A.

The remaining quantity of Metformin Hydrochloride, microcrystalline cellulose and croscarmellose sodium were weighed and dispensed. Metformin Hydrochloride was passed through mesh #20 to remove any lumps. Microcrystalline cellulose and croscarmellose sodium were passed through mesh #60 and added to Metformin Hydrochloride. It was blended for 2-3 min and stored in a tightly closed polybag as BLEND B.

Figure 2:
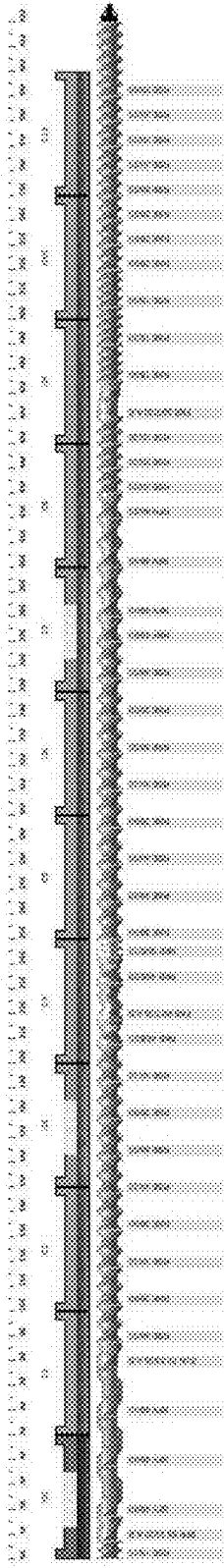
FIG. 2 illustrates the screw configuration of a co-rotating twin-screw processor in accordance with Example 2 of the present disclosure.

The blends were processed using a co-rotating twin-screw extruder (Omega 20) designed by the applicant herein with screw configuration F2 illustrated in FIG. 2. Two feeding systems were used for the feeding of two separate blends as mentioned above. BLEND A was fed at barrel 1 and BLEND B was fed at barrel 8. The feed rates were adjusted to about 80.0 g/min. Thus the total output was 160.0 g/min. Steam generated through steam generator was introduced at barrel 4. The screw design and processing parameters were as follows.

Processor Configuration

The trials were performed using a co-rotating twin-screw extruder (Omega 20) designed by the applicant herein. The machine specification and the process parameters are described in Table 6, below.

TABLE 6

Configuration of the Twin-screw Processor of Example 2

| Machine Name | Omega 20 |
|---|---|
| L/D | 60 |
| Total no. of Barrels | 12 |
| Screw speed | 800 rpm |

TABLE 6-continued

Configuration of the Twin-screw Processor of Example 2

| | |
|---|---|
| Element length | 1230 mm |
| Maximum Screw Speed | 1200 rpm |
| Maximum motor power | 7.5 kW |
| Diameter | 19.6 mm |
| Percentage of kneading blocks | 9.27% |
| Feed Rate | 80.0 g/min (at Barrel 1) |
| | 80.0 g/min (at Barrel 8) |
| Barrel Temperature | 30° C. |
| Steam Input | 2.5% w/w of input blend |

Screw Element

| | |
|---|---|
| 1. | RSE 15/15 |
| 2. | SFN 53, 33/20 A, B |
| 3. | SFV 40/40 |
| 4. | SFV 40/40 |
| 5. | SFV 40/40 |
| 6. | SVN 53, 33/20 A, B |
| 7. | RSE 30/30 |
| 8. | RSE 30/30 |
| 9. | RSE 30/30 |
| 10. | RSE 30/30 |
| 11. | RSE 30/30 |
| 12. | RSE 30/30 |
| 13. | RSE 30/30 |
| 14. | RSE 30/30 |
| 15. | RKB 45/5/20 |
| 16. | FKB 90/7/30 A, B |
| 17. | RKB 45/5/20 |
| 18. | NKB 90/5/15 |
| 19. | RSE 30/30 |
| 20. | RSE 30/30 |
| 21. | RSE 30/30 |
| 22. | RSE 30/30 |
| 23. | RSE 30/30 |
| 24. | RSE 30/30 |
| 25. | RSE 30/30 |
| 26. | RSE 30/30 |
| 27. | NRF 40/20 |
| 28. | RFV 40/40 |
| 29. | RFV 40/40 |
| 30. | RFN 40/20 |
| 31. | RSE 20/20 |
| 32. | RSE 20/20 |
| 33. | RSE 20/20 |
| 34. | FKB 30/7/30 A, B |
| 35. | RSE 15/30 |
| 36. | RSE 15/30 |
| 37. | RSE 15/30 |
| 38. | RSE 20/20 |
| 39. | RSE 20/20 |
| 40. | RSE 20/20 |
| 41. | RSE 20/20 |
| 42. | RSE 20/20 |
| 43. | RSE 20/20 |
| 44. | RSE 20/20 |
| 45. | RSE 20/60 |

Screw Configuration:

Screw Configuration F2 of the processor is provided in Table 7 below. Table 8 gives the Temperature profile.

TABLE 7

Screw configuration for L/D 60

Screw Elements

| | RSE-15/15 (CHS) | SFN 40/20 | SFV 40/40 | SVN 40/20 | RSE 30/30 | RKB 45/5/20 | FKB 90/7/30 | RKB 45/5/20 | NKB 90/5/15 |
|---|---|---|---|---|---|---|---|---|---|
| Nos. | 1 | 1 | 3 | 1 | 8 | 1 | 1 | 1 | 1 |

Screw Elements

| | RSE 30/30 | NRF 40/20 | RFV 40/40 | RFN 40/20 | RSE 20/20 | FKB 30/7/30 | RSE 15/30 | RSE 20/20 | RSE 20/10 | RSE 20/60 |
|---|---|---|---|---|---|---|---|---|---|---|
| Nos. | 8 | 1 | 2 | 1 | 3 | 1 | 3 | 7 | 1 | 1 |

TABLE 8

Barrel Temperature (° C.) Profile

| | B1 (C0) | B2 (C1) | B3 (C2) | B4 (C3) | B5 (C4) | B6 (C5) | B7 (C6) | B8 (C7) | B9 (C8) | B10 (C9) | B11 (C10) | B12 (C11) |
|---|---|---|---|---|---|---|---|---|---|---|---|---|
| Temp (° C.) | 30 | 30 | 30 | 30 | 30 | 30 | 30 | 30 | 30 | 30 | 30 | 30 |

TABLE 9

Different Zones of the Processor of Example 2

| | Barrel No. | | | | | | | | | | | |
|---|---|---|---|---|---|---|---|---|---|---|---|---|
| | B1 | B2 | B3 | B4 | B5 | B6 | B7 | B8 | B9 | B10 | B11 | B12 |
| (Temp ° C.) | 30 | 30 | 30 | 30 | 30 | 30 | 30 | 30 | 30 | 30 | 30 | 30 |
| Processing Zones | Input zone (Blend A) | | | Steam input | Granulation zone | Conveying zone | | Moisture Absorbent input (Blend B) | Moisture distribution zone | Conveying zone | | |

The Metformin Hydrochloride granules collected from the twin-screw processor were evaluated for attributes as given below.
Experimental Results:
1. Particle Size Distribution:

TABLE 10

Particle Size Distribution of Granules of Example 2

| Sieve no. | % Cumulative Wt. Retained |
|---|---|
| #120 | 33.79 |
| #170 | 72.25 |
| #270 | 92.61 |
| Base | 99.36 |

2. Granule Properties: Characterization of the granules was carried out by way of determination of Bulk Density, Tapped Density, Compressibility Index and Hausner's Ratio.

TABLE 11

Properties of granules of Example 2

| Parameters | Granules |
|---|---|
| Bulk density (g/cc) | 0.365 |
| Tapped Density (g/cc) | 0.548 |
| Compressibility index (%) | 33.33 |
| Hausner's Ratio | 1.500 |

Specific Embodiments are Described Below

A process for preparing granules in a co-rotating twin screw processor, comprising feeding an input material for granulation in the processor using one or more powder feeders, introducing steam as a granulation activating agent in the processor, granulating the input material in the presence of steam to form granules, and optionally, collecting the granules from a discharge zone of the processor, wherein feed rate of the steam into the processor is determined based on feed rate of the input material into the processor.

Such process(es), wherein 2.5 to 5 percent w/w of the steam with respect to the input material is introduced in the processor.

Such process(es), wherein the feed rate of the steam in the processor is adjusted based on the feed rate of the input material into the processor such that steam in an amount of about 2.5 to 5 percent w/w with respect to the input material is available for granulation.

Such process(es), wherein the feed rate of steam is constant for a fixed feed rate of the input material.

Such process(es), wherein the granules are collected from the processor without a moisture reduction step.

Such process(es), wherein the input material comprises at least one active ingredient.

Such process(es), wherein the input material comprises at least one binder.

Such process(es), wherein moisture content of the granules collected from the processor is not more than 5 percent w/w.

Such process(es) further comprising mixing uniformly, the granules discharged from the processor with a moisture absorbent.

Such process(es) further comprising adding at least one moisture absorbent into the processor after activation of the granulation of the input material with steam and before collecting the granules from the discharge zone of the processor.

Such process(es), wherein the moisture absorbent is selected from a group consisting of microcrystalline cellulose, silicon dioxide or a combination thereof.

Such process(es), wherein the moisture absorbent is microcrystalline cellulose having loss on drying not more than 1.5 percent w/w.

Further Specific Embodiments are Described Below

A co-rotating twin screw processor for preparing granules comprising an input zone having one or more powder feeders for feeding an input material into the processor, a steam feeder configured to introduce steam as a granulation activating agent in to the processor, a granulation zone for granulating the input material in the presence of steam to form granules, a controller configured to control operation and feed rate of at least one of the powder feeder or the steam feeder such that 2.5 to 5 percent w/w of the steam with respect to the input material is available for granulation, and a discharge zone having a non-extruding opening for collecting the granules.

Such processor(s), wherein the steam feeder is located in the granulation zone of the processor.

Such processor(s) further comprising an excipient feeder for introducing at least one moisture absorbent into the processor downstream of the steam feeder.

Such processor(s), further comprising a moisture distribution zone for mixing at least one moisture absorbent with the granules from the granulation zone to obtain the granules having moisture content not more than 5 percent w/w.

Such processor(s), wherein the controller is configured to control operation and feed rate of one or more of the powder feeder, the steam feeder or the excipient feeder such that moisture content of the granules obtained from the discharge zone is less than 5 percent w/w.

Such processor(s), wherein the controller is configured to adjust rate of introduction of the steam in the processor based on feed rate of the input material into the processor such that 2.5 to 5 percent w/w of the steam with respect to the input material is available for granulation.

Such processor(s), wherein the granulation zone comprises not more than two pairs of fractional kneading elements for uniform distribution of the steam during granulation.

Such processor(s), wherein the granulation zone comprises not more than two pairs of fractional kneading elements for uniform distribution of the steam during granulation.

Such processor(s), wherein the moisture distribution zone comprises at least one pair of fractional kneading element.

INDUSTRIAL APPLICABILITY

The process and processor disclosed provide for the continuous production of granules of the powder material with high granulation yields and desirable granule properties like ability to flow freely, compressibility, required particle size distribution and granule strength.

The process disclosed is scalable and suitable for rapid production of high volumes of uniform granules which are ready to be further processed into unit dosage forms like tablets and capsules.

Use of an optimal quantity of steam sufficient to granulate the powder material but not to over-wet it, combined with the twin screw processor configuration as disclosed, contributes in obtaining uniform sized dry granules without requiring a separate drying and/or milling step. The process results in high granulation yield. The granules obtained exhibit desirable properties like ability to flow freely, compressibility, required particle size distribution and granule strength. As additional drying or milling step are not required, the process is energy efficient and cost-effective.

The process can be effectively optimized for granulation of blend containing moisture sensitive and/or heat sensitive substances as it is carried out at low temperatures and with optimum moisture addition which is not more than 5% w/w.

The present disclosure provides an effective solution to address the previously mentioned problems in granulation technology. It departs from the use of conventional planetary mixers or high shear granulators thereby providing an alternative to batch processing and quasi-continuous processing.

Further, the disclosed process provides control over the ratio of granulating aid to the blend being granulated by introducing steam at a constant rate throughout the granulation process.

We claim:

1. A co-rotating twin screw processor for preparing dry granules comprising:
    an input zone having one or more powder feeders for feeding an input material into the processor;
    a steam feeder configured to introduce steam as a granulation activating agent in to the processor;
    a granulation zone for granulating the input material in the presence of steam to form granules;
    a controller configured to control operation and feed rate of at least one of the powder feeder or the steam feeder such that 2.5 to 5 percent w/w of the steam with respect to the input material is available for granulation; and
    a discharge zone having a non-extruding opening for collecting the dry granules.

2. The processor as claimed in claim 1, wherein the steam feeder is located in the granulation zone of the processor.

3. The processor as claimed in claim 1 further comprising an excipient feeder for introducing at least one moisture absorbent into the processor downstream of the steam feeder.

4. The processor as claimed in claim 3, wherein the controller is configured to control operation and feed rate of one or more of the powder feeder, the steam feeder or the excipient feeder such that moisture content of the dry granules obtained from the discharge zone is less than 5 percent w/w.

5. The processor as claimed in claim 1, further comprising a moisture distribution zone for mixing at least one moisture absorbent with the granules from the granulation zone to obtain the dry granules having moisture content not more than 5 percent w/w.

6. The processor as claimed in claim 5, wherein the moisture distribution zone comprises one pair of fractional kneading elements.

7. The processor as claimed in claim 1, wherein the controller is configured to adjust rate of introduction of the steam in the processor based on feed rate of the input material into the processor such that 2.5 to 5 percent w/w of the steam with respect to the input material is available for granulation.

8. The processor as claimed in claim 1, wherein the granulation zone comprises at least one fractional kneading element for uniform distribution of the steam during granulation.

9. The processor as claimed in claim 1, wherein the granulation zone comprises not more than two pairs of fractional kneading elements for uniform distribution of the steam during granulation.

* * * * *